United States Patent
Chan et al.

(10) Patent No.: US 9,693,707 B2
(45) Date of Patent: Jul. 4, 2017

(54) OPTICAL SHAPE SENSING FIBER FOR TIP AND SHAPE CHARACTERIZATION OF MEDICAL INSTRUMENTS

(75) Inventors: Raymond Chan, San Diego, CA (US); Robert Manzke, Eindhoven (NL); Aleksandra Popovic, New York, NY (US); Gert Wim 'T Hooft, Eindhoven (NL); Heinrich Von Busch, Aachen (DE)

(73) Assignee: Koninklijke Philips N.V., Eindhoven (NL)

(*) Notice: Subject to any disclaimer, the term of this patent is extended or adjusted under 35 U.S.C. 154(b) by 237 days.

(21) Appl. No.: 13/981,336

(22) PCT Filed: Jan. 25, 2012

(86) PCT No.: PCT/IB2012/050339
§ 371 (c)(1),
(2), (4) Date: Jul. 24, 2013

(87) PCT Pub. No.: WO2012/101584
PCT Pub. Date: Aug. 2, 2012

(65) Prior Publication Data
US 2013/0310685 A1    Nov. 21, 2013

Related U.S. Application Data

(60) Provisional application No. 61/437,048, filed on Jan. 28, 2011.

(51) Int. Cl.
*A61B 5/05* (2006.01)
*A61B 5/06* (2006.01)
(Continued)

(52) U.S. Cl.
CPC .............. *A61B 5/061* (2013.01); *A61B 34/20* (2016.02); *G01B 11/18* (2013.01);
(Continued)

(58) Field of Classification Search
CPC ........ A61B 19/5244; A61B 2019/5261; A61B 5/06; A61B 34/77
(Continued)

(56) References Cited

U.S. PATENT DOCUMENTS 5,973,317 A    10/1999  Hay
8,989,528 B2 *  3/2015  Udd ........................ A61B 5/06
                                                      385/10

(Continued)

FOREIGN PATENT DOCUMENTS

| CN | 101476879 A | 7/2009 |
| JP | 2003098037 A | 4/2003 |
| WO | WO2009155325 | 12/2009 |

*Primary Examiner* — Joel Lamprecht

(57) ABSTRACT

A shape sensing device, system and method include an interventional instrument (102) having regions of articulation to be configured to change shape during an interventional procedure. An optical fiber (202) is disposed on or about the areas of articulation in a pattern to provide an optical signal indicating an instantaneous change or current position or orientation of the instrument. A signal interpretation module (115) is configured to receive the optical signals and interpret the instantaneous change or current position or orientation of the instrument.

15 Claims, 5 Drawing Sheets

(51) Int. Cl.
  *G01B 11/16*   (2006.01)
  *G01D 5/353*   (2006.01)
  *A61B 34/20*   (2016.01)
  *A61B 34/30*   (2016.01)

(52) U.S. Cl.
  CPC .......... *G01D 5/35345* (2013.01); *A61B 34/30* (2016.02); *A61B 2034/2061* (2016.02)

(58) Field of Classification Search
  USPC ................................................ 600/182, 424
  See application file for complete search history.

(56) References Cited

U.S. PATENT DOCUMENTS

| | | |
|---|---|---|
| 2001/0021843 A1 | 9/2001 | Bosselmann et al. |
| 2007/0156019 A1 | 7/2007 | Larkin et al. |
| 2010/0030063 A1 | 2/2010 | Lee et al. |
| 2010/0048998 A1 | 2/2010 | Younge et al. |
| 2011/0090486 A1* | 4/2011 | Udd .............................. 356/73.1 |

* cited by examiner

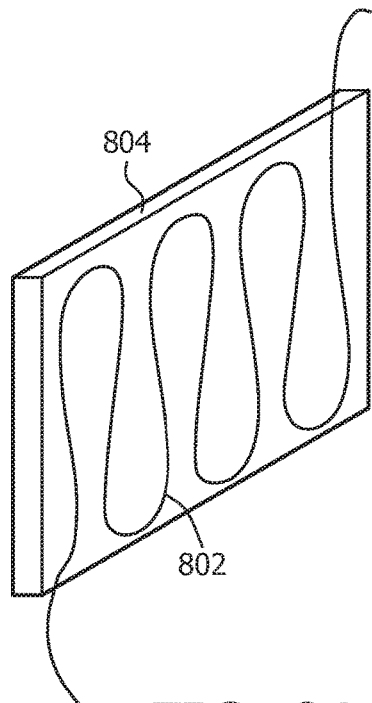 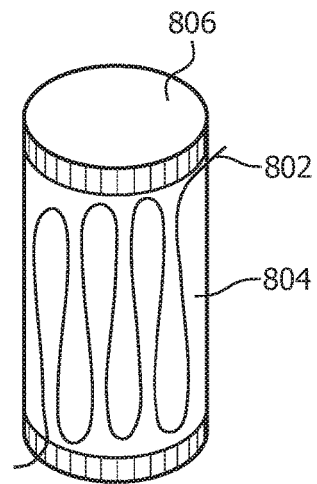
FIG. 8A  FIG. 8B
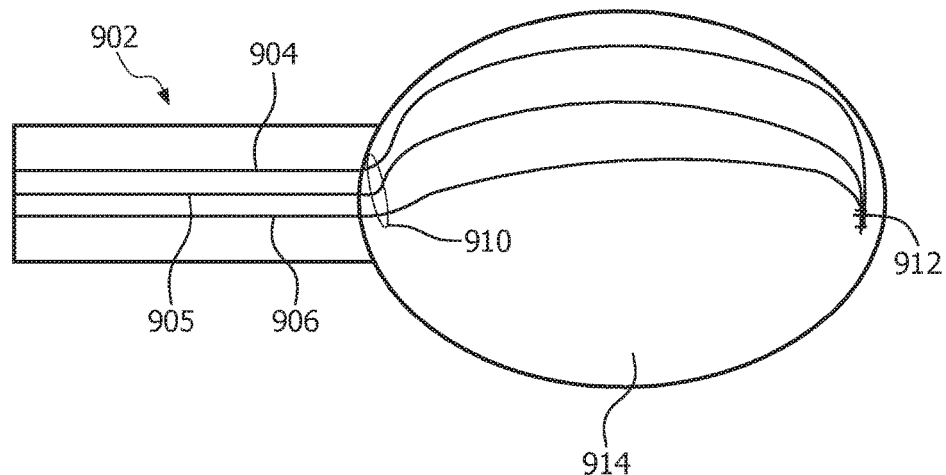
FIG. 9

OPTICAL SHAPE SENSING FIBER FOR TIP AND SHAPE CHARACTERIZATION OF MEDICAL INSTRUMENTS

CROSS-REFERENCE TO PRIOR APPLICATIONS

This application is the U.S. National Phase application under 35 U.S.C. §371 of International Application No. PCT/IB2012/050339, filed on Jan. 25, 2012, which claims the benefit of U.S. Application Ser. No. 61/437,048, filed on Jan. 28, 2011. These applications are hereby incorporated by reference herein.

This disclosure relates to shape sensing of medical instruments, and more particularly to a system, device and method for optical sensing of medical instruments.

The ability to accurately sense a tip and shape of a medical instrument or device plays an important role in interventional guidance. Optical shape sensing has been employed to provide instrument tracking technology, or for clinical applications in which optical shape sensing can be employed. However, the manner of attachment of the optical sensing device to an instrument plays a role in how optical shape sensing performs in different clinical applications.

Shape sensing may be based on fiber optic Bragg grating sensors. A fundamental principle behind the operation of a fiber Bragg grating (FBG) is Fresnel reflection at each of the interfaces where the refractive index is changing. For some wavelengths, the reflected light of the various periods is in phase with others so that constructive interference exists for reflection and consequently, destructive interference for transmission. The Bragg wavelength is sensitive to strain as well as to temperature. This means that Bragg gratings can be used as sensing elements in fiber optical sensors.

As an alternative to fiber optic Bragg gratings, the inherent backscatter in conventional optical fiber can be exploited. One such approach is to use Rayleigh scatter in a standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in 3 or more cores running within a single length of multicore fiber, the 3D shape and dynamics of the surface of interest would be trackable.

When an optical fiber is attached along the length of a catheter, it terminates abruptly at the tip of the distal end. In this configuration, backscattering due to reflections at the tip interface can interfere with the desired optical grating signal. In practice, this results in signal corruption that prevents tracking up to the very tip of the fiber, resulting in shape measurements only up to a point several millimeters or centimeters away. While coupling the tip of the fiber with index matching gel to dissipate light out into the surrounding tissue medium to help to reduce backreflection effects is workable in a laboratory, it can complicate manufacturing of medical grade products. Furthermore, it is only a partial solution since the optimal refractive index of the coupling gel depends on the tissue that the instrument operates within (e.g., air versus blood).

Conventional approaches of running a multicore fiber straight along the length of an instrument cannot take advantage of error characterization compensation opportunities that could be provided by an attachment configuration for the fiber on the catheter.

In applications involving highly dynamic devices, such as rigid robots (e.g., robots with a few clearly differentiated joints and rigid segments between the joints) or continuum robots (e.g., robots having plurality of joints or segments capable of taking a continuous snake-like form), the problem of sensing at the tip of a medical device is accompanied by difficult and potentially error-prone mounting. In rigid robots, the fiber has to be anchored at joints to avoid buckling that may cause error in position reading. Anchoring of fiber can cause other problems, such as unwanted axial strain and excess force that may damage the fiber. In continuum robots, fibers are usually placed along the robot's backbone, thus failing to measure elastic deformation of segments of the robot. Since shape sensing plays an important role in the control loop of continuum robots, small deformation errors can propagate and cause large displacements at the tip.

Active devices or robots can have motors/encoders that are not autoclavable. In such cases, the robot is draped with a thin polymer film to protect moving parts. The draping is usually disposable. Measuring the shape along the backbone of the robot does not take the deformation of the draping into account. This may cause collisions with structures or irritation of tissue due to contact with the draping.

In accordance with the present principles, a shape sensing device, system and method include an interventional instrument having regions of articulation to be configured to change shape during an interventional procedure. An optical fiber is disposed on or about the areas of articulation in a pattern to provide an optical signal indicating an instantaneous change or current position or orientation of the instrument. A signal interpretation module is configured to receive the optical signals and interpret the instantaneous change or current position or orientation of the instrument.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein:

FIG. 8A is a perspective view of a sheet or film including a fiber in accordance with one illustrative embodiment;

FIG. 8B is a perspective view of a robot segment having the sheet of FIG. 8A disposed thereon in accordance with one illustrative embodiment;

FIG. 9 is a perspective view of a volume forming instrument having meridian fiber segments disposed thereon or therein in accordance with one illustrative embodiment.

Figure 1:
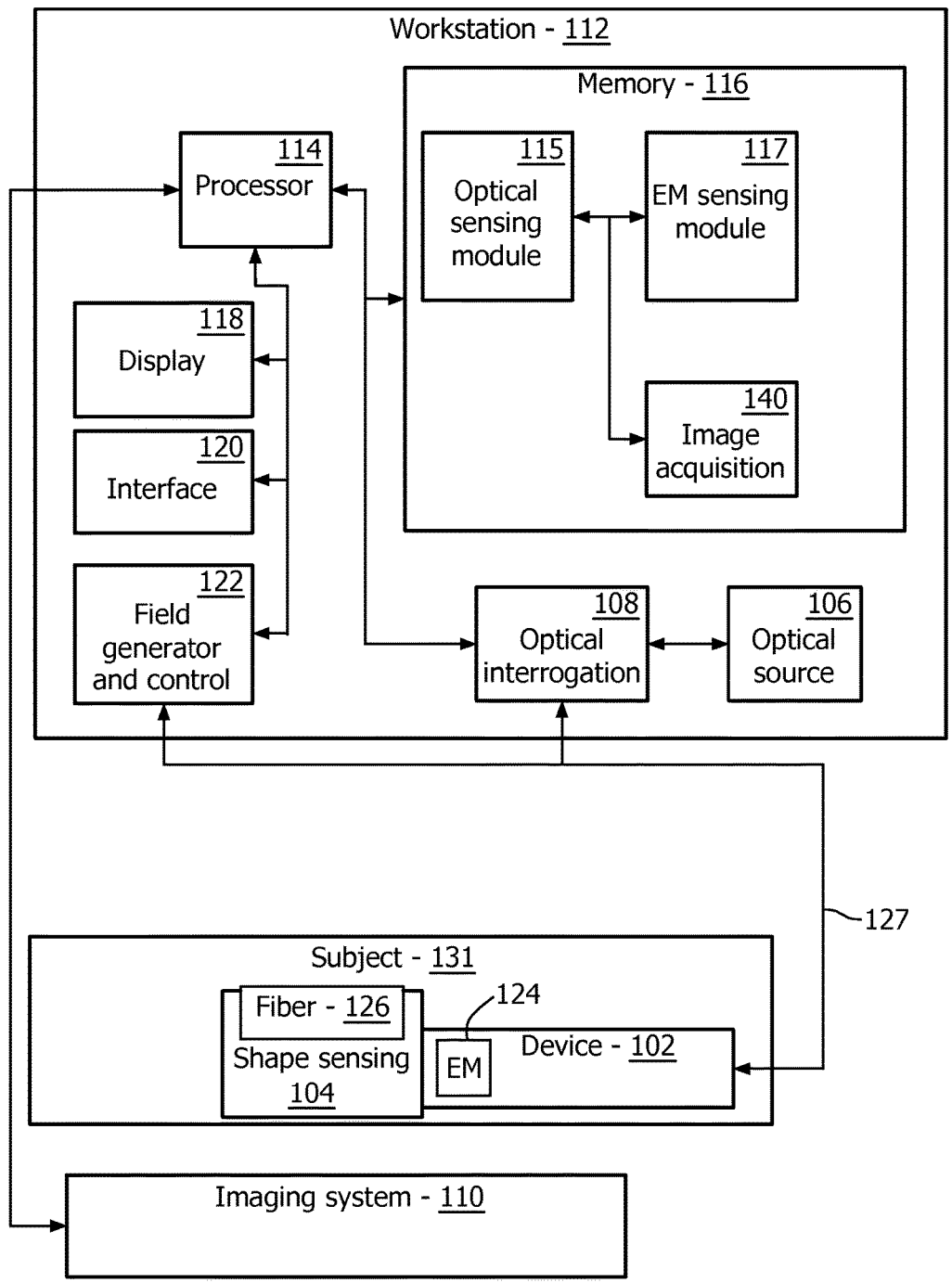
FIG. 1 is a block/flow diagram showing a system/method for performing a procedure with optical shape sensing of a medical instrument in accordance with the present principles.

In accordance with the present principles, fiber attachment configurations or geometries are exploited to obtain a "built-in" mechanism for detection and correction/calibration of shape tracking errors. Straightforward attachment along the instrument length does not lend itself to error characterization and subsequent correction. In addition, arrangements for fiber attachments are provided that eliminate backscatter corruption in addition to error characterization. Fiber attachment configurations are provided for highly dynamic devices, such as, rigid robots (e.g., robots with a few clearly differentiated joints and rigid segments between the joints) or continuum robots (e.g., robots having a plurality of joints or segments) for which the problem of sensing at the tip of optical sensor is accompanied by difficult and potentially error-prone mounting.

In particularly useful embodiments, optical sensing devices and systems include an optical fiber or a set of optical fibers incorporated into an instrument, together with an optical interface/connector to permit backloading over the instrument (e.g., guidewire-like configurations). An optical interrogation console includes a processor that implements a shape determination program or method that permits a tip location and shape of the instrument, as well as measurement error and confidence intervals to be determined intra-procedurally. An electromagnetic (EM) tracking console or other position and orientation sensing technology may optionally be employed to augment localization measurements from fiber optic shape sensing. The EM tracking console may include a sensor coil and field generator for hybrid tracking functionality (e.g., EM and optical sensing). In one embodiment, an imaging system for hybrid functionality may be employed.

The optical fibers may be attached to the instrument in a known or predetermined geometry (e.g., a patterned rosette or helical windings of sensing fiber at intervals along the fiber length) to permit "live" interrogation of tracking errors and calibration for a starting "reference" position and fiber launch direction. The optical fibers may also be attached to the instrument so as to form a continuous loop/path at the instrument tip. This permits optical signals to return to the interrogation console along a separate fiber path, eliminating the need for fiber termination at the instrument tip. Forward and return paths of the optical fiber sensors permit redundant/additional measurements of instrument shape. The shape determination or reconstruction program accounts for forward and return path optical signal calibration, characterization, and reconstruction to produce improved measurement robustness and performance.

In one embodiment, a data connection between the optical shape sensing platform and a tracking (e.g., EM) or imaging platform may be provided to permit additional information about fiber behavior to be used in improving navigation/tracking performance in real-time.

It also should be understood that the present invention will be described in terms of medical instruments; however, the teachings of the present invention are much broader and are applicable to any instruments employed in tracking or analyzing complex biological or mechanical systems. In particular, the present principles are applicable to internal tracking procedures of biological systems, procedures in all areas of the body spanning endovascular, endoluminal, interstitial, and intracellular domains in regions of interest including but not limited to the lungs, gastro-intestinal tract, excretory organs, neural structures, heart, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

Referring now to the drawings in which like numerals represent the same or similar elements and initially to FIG. 1, a system 100 for performing a medical procedure is illustratively depicted. System 100 may include a workstation or console 112 from which a procedure is supervised and/or managed. Workstation 112 preferably includes one or more processors 114 and memory 116 for storing programs and applications. Memory 116 may store an optical sensing module 115 configured to interpret optical feedback signals from a shape sensing device 104. Optical sensing module 115 is configured to use the optical signal feedback (and any other feedback, e.g., EM) to reconstruct deformations, deflections and other changes associated with a medical device or instrument 102 and/or its surrounding region. The medical device 102 may include a catheter, a guidewire, a probe, an endoscope, a robot, an electrode, a filter device, a balloon device, or other medical component, etc.

The shape sensing device 104 includes one or more optical fibers 126 which are coupled to the device 102 in a set pattern or patterns. The optical fibers 126 connect to the workstation 112 through cabling 127. The cabling 127 may include fiber optic, electrical and instrumentation, etc., as needed.

Workstation 112 may include a display 118 for viewing internal images of a subject 131 if an imaging system 110 is employed. Imaging system 110 may include a magnetic resonance imaging (MRI) system, a fluoroscopy system, a computed tomography (CT) system, etc. Display 118 may also permit a user to interact with the workstation 112 and its components and functions, or any other element within the interventional system 100. This is further facilitated by an interface 120 which may include a keyboard, mouse, a joystick, a haptic device, or any other peripheral or control to permit user feedback from and interaction with the workstation 112.

System 100 may include an EM tracking or similar position or orientation sensing system which may be integrated with the workstation 112 or be a separate system. The EM tracking system includes an EM sensing module 117 used to interpret EM signals generated by the medical device 102 during a procedure. The medical device 102 may include one or more EM tracking sensors 124, which may be mounted on the device 102. A field generator and control module 122 may include one more coils or other magnetic field generation sources employed in tracking applications. The medical device 102 will include a fiber optic shape sensing tether device 104 which provides optical readings that are reconstructed into information about device location, orientation, and shape.

The EM sensing module 117 and the optical sensing module 115 may be employed with an image acquisition module 140 to acquire and display internal images of a procedure or otherwise assist in tracking the activities of the procedure.

Workstation 112 interacts with an optoelectronic console which includes an optical source 106 to provide optical fibers with light. An optical interrogation unit or module 108 is employed to detect light returning from all fibers. This permits the determination of strains or other parameters, which will be used to interpret the shape, orientation, or other characteristics, sensed by the interventional device 102. The light signals will be employed as feedback to make adjustments to access errors and to calibrate the device 102 or system 100.

Shape sensing device 104 includes one or more fiber attachment configurations which are adapted to exploit their geometry to obtain a "built-in" mechanism for detection and correction/calibration of shape tracking errors. The arrangement configurations eliminate backscatter corruption and provide error characterization features. Fiber attachment configurations are provided for dynamic devices, such as, rigid robots (e.g., robots joints and rigid segments between the joints) or continuum robots (e.g., robots having a plurality of segmented joints) for which the problem of sensing at the tip of optical sensor is accompanied by difficult and potentially error-prone mounting.

Optical interrogation module 108 works with optical sensing module 115 (e.g., shape determination program) to permit a determination of a location and orientation of a tip as well as shape of the instrument or device 102. Measurement error and confidence intervals are determined intra-procedurally and provided as visual feedback to the operator for further optimization steps to be taken (including but not limited to changes in operator manipulation of the device, changes to the processing algorithm, or changes to the measurements used for processing). The optical fibers of shape sensing device 104 may be attached to the instrument 102 in a known or predetermined geometry (e.g., a patterned rosette or helical windings of sensing fiber at intervals along the fiber length) to permit "live" interrogation of tracking errors and calibration for a starting "reference" position and fiber launch direction.

The optical fibers may be attached to the instrument 102 so as to form a continuous loop/path at the instrument tip. This permits optical signals to return to the interrogation module 108 along a separate fiber path, eliminating the need for fiber termination at the instrument tip. Forward and return paths of the optical fiber sensors permit redundant/additional measurements of instrument shape. The shape determination or reconstruction program 115 accounts for forward and return path optical signal calibration, characterization and reconstruction to produce improved measurement robustness and performance. In one embodiment, the optical shape sensing module 115, EM sensing module 117 and any other tracking or imaging platform 110 may cooperate to permit additional information about fiber behavior to be used in improving navigation/tracking performance in real-time.

Figure 2:
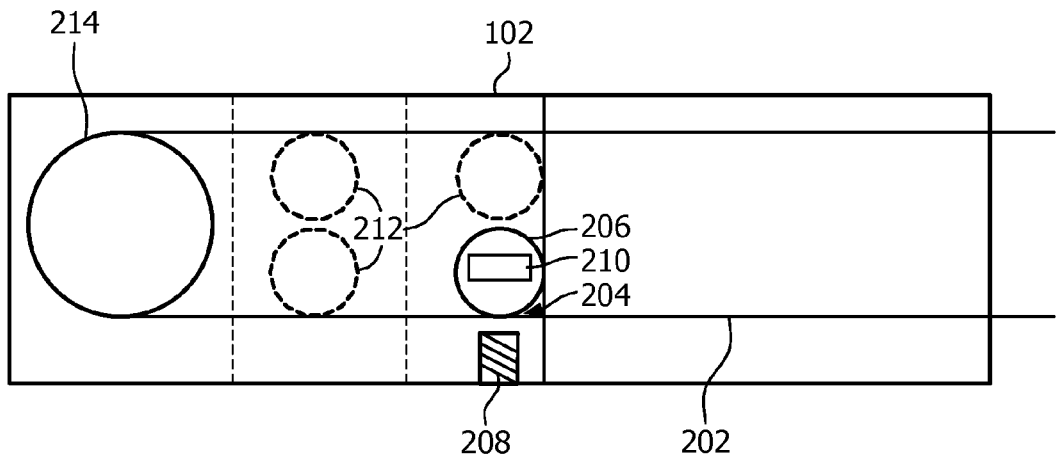
FIG. 2 is a diagram of a medical instrument having start position sensing in accordance with particularly useful embodiments.

Referring to FIG. 2, an exemplary embodiment of a shape sensing fiber 202 is illustratively depicted in accordance with one embodiment. The shape sensing fiber 202 is attached to an elongated instrument (e.g., device 102) in such a manner as to provide a calibration pattern of known geometry at the fiber tracking start point 204 to provide information about a reference origin and fiber launch orientation. In the present example, a fiber loop 206 is employed to determine a start position or point 204. Shape estimation may be performed taking into account the known calibration geometry to permit for detection, quantification, and correction of shape errors that are introduced during an interventional procedure. For example, if device 102 includes a catheter, deflections and orientations of the catheter can be determined using one or more shape sensing fibers 202. The geometry of the fiber 202 relative to the device 102 as well as relative to the fiber itself are both employed (along with other data) to determine changes and errors due to movements and usage of the device 102.

In one embodiment, the shape sensing calibration pattern is further augmented with one or more sensors 208, e.g., a miniature EM sensor coil, at the origin point 204 to obtain further information about the fiber tracking start point 204 and orientation. In this way, hybrid optical shape sensing and EM based localization are available to pinpoint changes in the device 102.

In another embodiment, the shape sensing calibration pattern is further augmented with optical, photoacoustic, or other imaging visible markers 210 to permit for further information from optical tracking or other available imaging information about the fiber tracking start point 204 and orientation. In this way, hybrid optical shape sensing and imaging based localization are provided. EM tracking and other techniques may be used as well. Further, any combination of these techniques may be employed to further support the fiber sensing pattern localization.

In another embodiment, multiple calibration patterns may be repeated at defined intervals along the fiber length to permit for automatic detection, characterization, and correction for any shape errors that may accumulate over fiber segments or portions. FIG. 2 illustratively shows additional fiber loops 212 optionally spaced apart along the length of fiber 202. An additional larger loop 214 is provided at a distal end portion of the device 102. This may provide additional information from the tip of the device 102. In all cases, the configuration geometry provides a constraint or constraints that can be used to validate shape estimates and, if needed, to correct for erroneous reconstructions.

Figure 3:
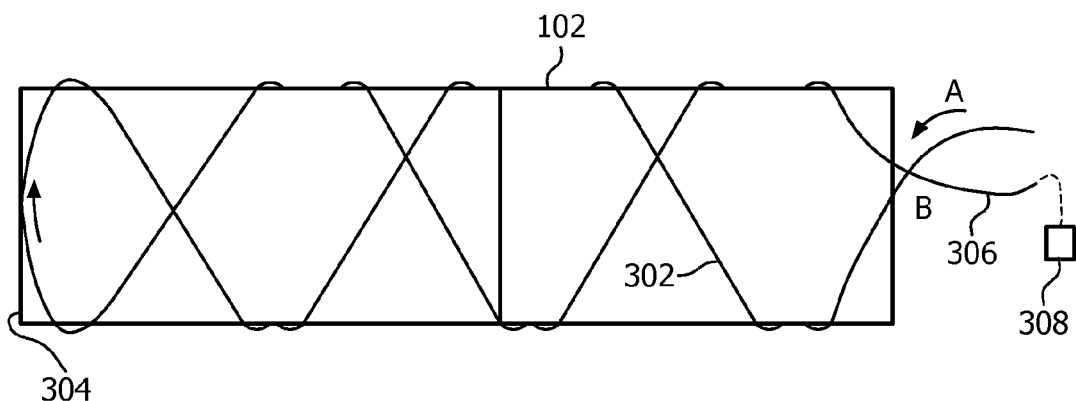
FIG. 3 is a diagram of a medical instrument having forward and reverse path optical sensing in accordance with a particularly useful embodiment.

Referring to FIG. 3, another embodiment includes a fiber 302 that is wrapped about the device 102 such that a forward shape sensing fiber path "A" is looped around a tip 304 of the device 102 in such as way as to form a return path "B" towards the interrogation module 108 in workstation 112 (see FIG. 1). An end of the return fiber 306 can be coupled to a photodetector 308 (e.g., at the optical interrogation module 108) for measurement of the transmitted optical signal (forward transmitted light) for additional measurements to be used in shape reconstruction. Forward transmitted light can be measured, augmenting the observations available from a backreflected optical signal that is normally used for fiber shape interrogation. It should be understood that the fiber 302/306 may be mounted internally in the device 102 or the device 102 with fibers may be covered with a sheath or the like.

While the backreflected signal traveling through a single fiber path has particular advantages due to automatic compensation for birefringence (reducing the need for adjustment of polarization controls as fiber shape changes) and better signal to noise characteristics than the forward transmitted light, measurements of the forward transmitted signal represent additional optical information that can be exploited to improve shape tracking performance. In other words, light reflected back down path A is measured as well as light traveling from path A to path B to provide additional information about the device 102, its position, orientation, errors, etc.

Shape reconstruction could also be performed on the forward path, the backward fiber path or both by setting corresponding shape calculation reference points. In the case where the entire or segmental shape data of the forward and backward paths are calculated, this information together with the known start and end reference locations of the fiber path can be used for mutual path error correction (since the path may form a loop at start and end points connected at the console or workstation 112). Starting from a known reference point, errors in shape calculation would accumulate towards the end of the segment. If multiple known reference points are exploited for computations using the forward and backward optical paths, relative shape can be reconstructed with high accuracy. Absolute shape may be also be calculated based on the availability of high accuracy relative shape segments which overlap or interleave with one another, starting from a known reference position (e.g., the fiber start reference point or fiber end termination point within the interrogation console).

Another factor is the selection of optimal laser parameters, such as wavelength sweep frequency, bandwidth and step size for such extended fiber length applications. These parameters need to be achievable with available laser sources and need to be chosen to obtain sufficiently high measurement resolution over the extended length for accurate shape calculation. As an alternative, the light transmitted through the return path can be coupled into an optically absorbing medium within the interrogation module 108 (as opposed to a coupling medium at the instrument tip which presents issues as previously described). With plastic optical fiber that permits tight bending radii, the forward and return paths can be formed with tight radii of curvature, allowing for use within interventional instruments with small tip diameters.

Figure 4:
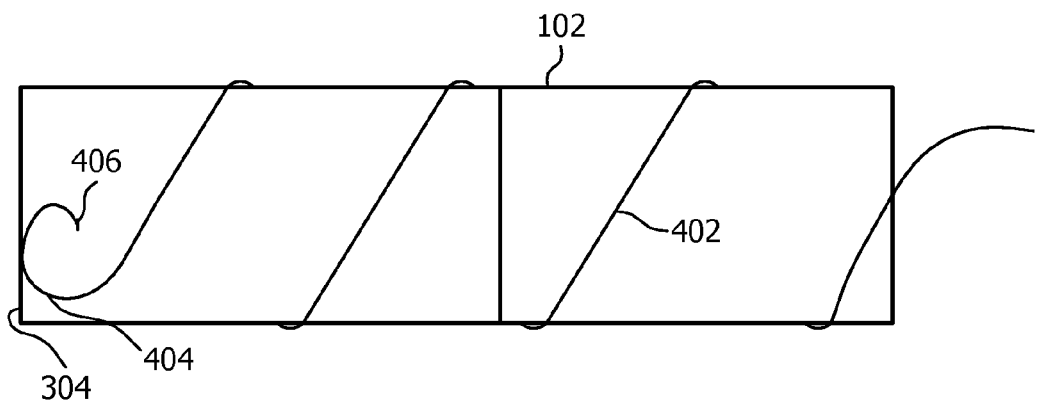
FIG. 4 is a diagram of a medical instrument having a tightly radiused and terminated end portion to determine a tip of the instrument in a particularly useful embodiment.

Referring to FIG. 4, in cases where measurement of the forward transmitted signal is not desired, an alternative mechanical method to eliminate Fresnel reflection at the tip 304 is to form a tight loop 404 in fiber 402 at the end of the device 102, with a radius of curvature that is sufficiently small to induce large optical losses in fiber 402. For the example of a catheter, the fiber 402 is configured in a set pattern along its length, and the fiber 402 can be looped to form a small (semi)circle at its distal tip and then just end, preferably with an angle polished interface 406 at the end of the loop 404.

Figure 5:
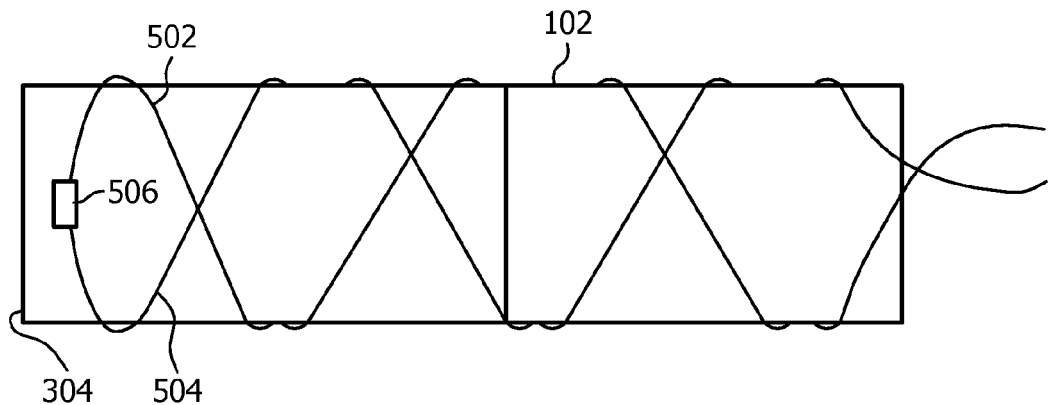
FIG. 5 is a diagram of a medical instrument having a splitter joining two fiber segments in accordance with a particularly useful embodiment.

Referring to FIG. 5, in another embodiment, single core optical fibers 502 and 504 can be mounted on an elongated device 102 following a defined path or geometry. At the distal end 304 of the device 102, the fibers 502 and 504 can be connected using a fiber-based beam splitter 506, or two or more single-core fibers can be placed forward and backward along the elongated device (as in FIG. 2), where at the distal tip the radius of curvature of the fiber 202 (FIG. 2) is limited by the minimum bend angle of the optical fiber (e.g., 15 times the total fiber diameter, i.e. 2.25 mm for a 150 micron fiber). This models a multi-core fiber setup, but with larger inter-fiber separation. Strain sensing can now be performed on the forward and backward path of each single-core fiber and since their baseline geometric relationships are known, shape can be calculated from those strain values. Shape can also be computed from the single-core strain values in combination with an appropriate inverse model relating the deformable geometry with the strain measurement distribution and orientation. The setup would also offer the advantage that smaller minimum radii are possible at the distal end given the smaller diameter of the single-core fibers (compared with a multi-core shape sensing fiber).

Figure 6:
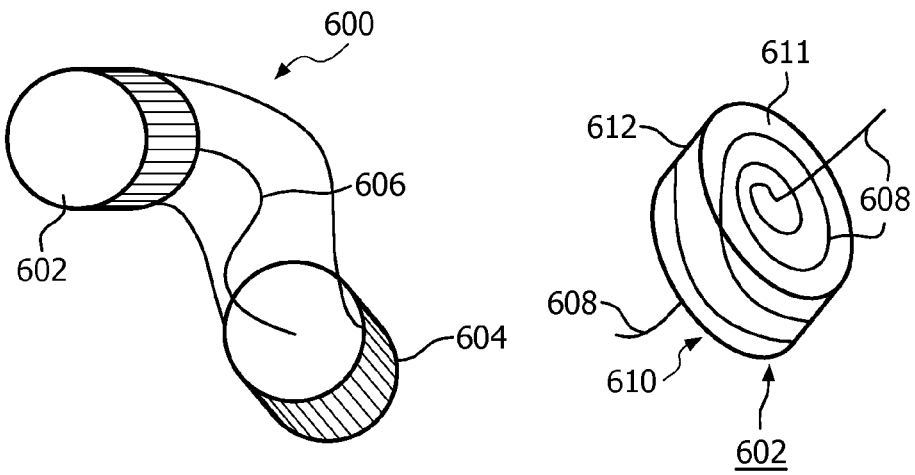
FIG. 6 is a perspective view showing a segment portion of a robot and a disk thereof in greater detail having a fiber pattern disposed within the disk in accordance with a particularly useful embodiment.

Referring to FIG. 6, a portion 600 of a continuum robot is illustratively shown. The continuum robot design 600 has axially oriented rigid parts, 602 and 604, connected with one or more backbones 606. An optical fiber 608 may be wrapped in a spiral on both faces 610, 611 and side 612 of the rigid parts 602 or 604 (for example, a disk) such that the spiral winds outward from the center of the distal face of the disk or part 602, loops around the side 612, and winds inward toward the center of the proximal face 611 of the disk 602. The fiber 602 can be placed in the backbone 606 between the disks 602 and 604. Ridges or other mechanical features for fiber placement can be provided. The fiber 606 can also be wound back to interrogation module 108 as described in previous embodiments.

Part of the fiber 606 wrapped around rigid part 602 serves as an indicator of compromised sensing, given that the exact shape of the spiral windings is known and is not changing. Advantages include that the shape is sensed along the center as well as on the sides of the robot 600, and the fixed arrangement on the sides 612 of the robot (as well as other places on the robot 600) permits error measurement and control.

Figure 7:
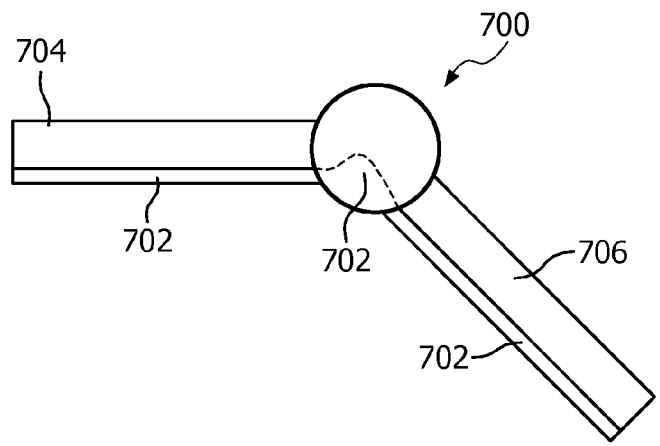
FIG. 7 is a diagram showing a joint portion of a robot having a fiber disposed within the joint in accordance with a particularly useful embodiment.

Referring to FIG. 7, a rigid robot joint 700 is illustratively shown. An optical fiber 702 is placed in a channel or channels formed in or on the surface of the robot or through the body of robot, in all areas excluding joints. Optical fibers 702 are loose in the air (or in a protective sheet made of polymers or similar materials) in the area of joints. A length of optical fiber in the joints is at least equal to the maximum extension of the joint, to avoid tearing and buckling as the robot is moving. In this configuration, shape is not being sensed in the joints. However, given that the robot has rigid segments 704, 706, knowing a position of the segments can give a full position of the entire robot. The fiber(s) can be arranged in known geometrical patterns. Advantages of this approach include sense shaping of a rigid robot without explicitly sensing the joint region to allow for simple mounting and maintenance. Axial strain in the joints is avoided, and geometrical patterns permit testing for errors in the optical sensing.

Referring to FIGS. 8A and 8B, particularly for continuum and rigid robot designs, fibers 802 can be embedded in a thin polymer sheet 804 (FIG. 8A) using known manufacturing methods. For example, optical fibers 802 can be embedded in, e.g., Polydimethylsiloxane (PDMS), a silicon-polymer with elasticity similar to that of human skin, although other materials may be employed. The pattern of embedded fiber 802 may include spiral windings, zig-zag patterns, etc. The sheet 804 can be wrapped around a robot body 806 (FIG. 8B) and attached to non-movable parts of the robot. For example, in continuum robots, the film 804 can be attached between a most distal and a most proximal rigid part. A disposable or autoclavable surgical end-effector may be coupled to the most distal part of the robot so it does not need draping. Additionally, the polymer film 804 can have a unique draping position to allow tracking of rotation of the robot. For example, top and bottom parts of the film can have holes (not shown) that uniquely fit pins on the robot's rigid parts. Advantages of this approach may include that shape is sensed around the robot, allowing for precise collision avoidance. A disposable sheet 804 simplifies maintenance of the robot.

It should be understood that FIGS. 8A and 8B include a serpentine fiber pattern, but other patterns may be employed including loops or different shapes, fiber crossovers, fiber borders, etc. It should be further understood that the film or sheet 804 may be customized to include different shapes or features to be applied to segments or rigid parts of products instead of or in addition to robots.

Referring to FIG. 9, for sensing of the shape, size, and orientation of volume-forming instruments 902, such as balloon catheters or brachytherapy devices with multiple channels, fibers 904, 905, 906 running meridian-like from a first "pole" 910 to a second "pole" 912 of an expandable/contractible volume 914 can be bundled at the poles, thereby providing, in such bundles, multiple fiber sections known to have identical shape and only small lateral displacements from each other (e.g., on the order of a fiber diameter). Compared to fiber arrangements without sections of fixed relative shape and position, the redundancy in shape/localization information in the pole bundles allows a reduction of fiber shape sensing errors in the meridian fiber sections as well as a more precise estimate of the shape, size, and orientation of the instrument. The meridian fiber sections can be connected in series, with one meridian fiber section looping back into another one at the end of a pole bundle, or embodied with separate shape sensing fibers (as shown in FIG. 9) in configurations covered in the above described embodiments.

It should be understood that the embodiments described herein can be combined with any other embodiments to achieve the desired aspects of the present principles. The present embodiments enable real-time characterization of any elongated instrument for procedural interventions, in which the shape or configuration of the device is needed for improving the accuracy of navigation/targeting.

Figure 10:
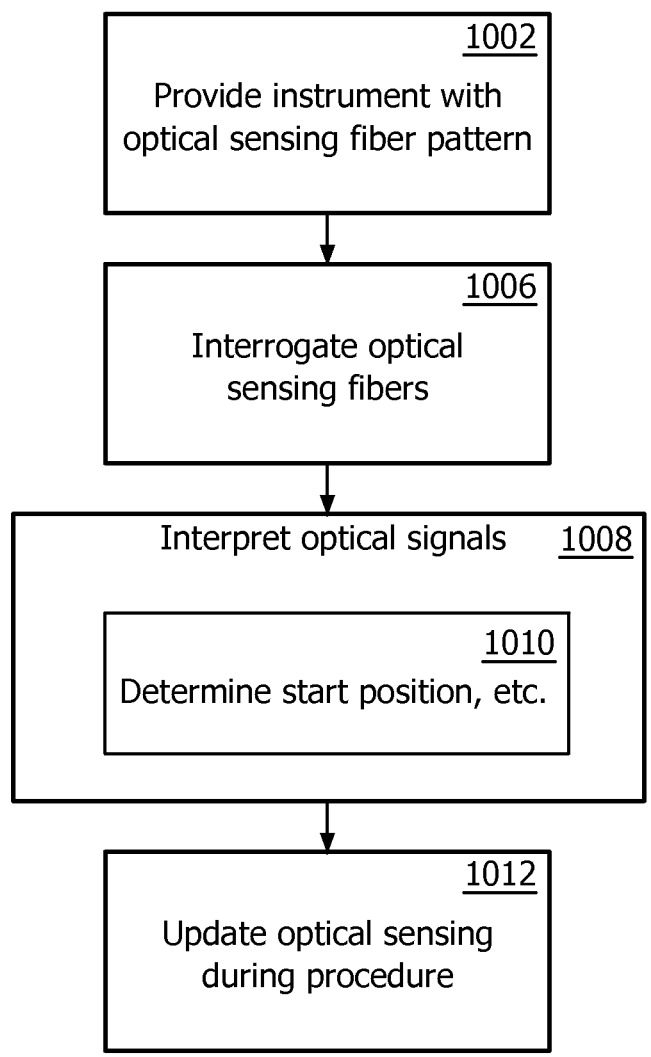
FIG. 10 is a block/flow diagram showing a method for performing optical shape sensing of a medical instrument in accordance with one illustrative embodiment.

Referring to FIG. 10, a block/flow diagram illustratively shows a method for shape sensing of a medical device. In block 1002, an interventional instrument is provided having one or more regions of articulation with one or more optical fibers disposed in a pattern on or about the one or more regions of articulation of the instrument. The interventional instrument may be a robot that may include one or more rigid segments, and the one or more optical fibers being disposed within the one or more rigid segments or that may include a joint and the one or more optical fibers being disposed within members connected by the joint.

The one or more optical fibers may be disposed within a flexible sheet, the flexible sheet being coupled to the instrument for sensing shape on the instrument. The instrument may include a volume-forming portion and the one or more optical fibers may be bundled at poles for sensing a shape of the portion.

The fibers may be configured in many set patterns and orientations as described herein. For example, the optical fibers may include two or more fiber segments on or in the instrument where the fiber segments are coupled with a splitter at a tip of the instrument such that an optical loss at the splitter indicates the tip. Another example includes providing a fiber terminated at a tip of the instrument such that an optical loss in fiber indicates the tip.

In block 1006, the one or more optical fibers are interrogated (e.g., using an interrogation module and source) to provide optical signals indicating an instantaneous change or current position or orientation of the instrument. Errors are also deciphered based upon additional data or positional comparisons and calibrations.

In block 1008, the optical signals received are interpreted to define the instantaneous change, current position or orientation of the instrument and calibrations errors. The optical signal may be interpreted using a returned forward signal and backreflections. Other functions may include EM tracking, imaging, etc. to confirm or augment optical data collected. The interpreting includes determining a start and/or end position where monitoring of the instrument begins in block 1010.

In block 1012, during a medical procedure, the instruments, position, orientation, calibration, error, etc. are updated and reported to a user in-real-time so that decisions may be made regarding the procedure and planning a next action.

In interpreting the appended claims, it should be understood that:

a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for devices, systems and methods for optical shape sensing fiber for tip and shape characterization of medical instruments (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A shape sensing device, comprising:
an interventional instrument having one or more regions of articulation to be configured to change shape during an interventional procedure;
one or more optical fibers coupled to the interventional instrument on or about the areas of articulation in a known geometric pattern such that the known geometric pattern permits detection of shape tracking errors, the one or more optical fibers providing an optical signal indicating an instantaneous change or current position or orientation of the instrument; and
a signal interpretation module configured to receive the optical signals and interpret the instantaneous change, current position or orientation of the instrument and the shape tracking errors.

2. The device as recited in claim 1, wherein the one or more optical fibers are disposed on or in the instrument and the optical signal includes a return signal and backreflections.

3. The device as recited in claim 1, wherein the one or more optical fibers include two fiber segments on or in the instrument and the fiber segments are coupled with a splitter at a tip of the instrument such that an optical loss at the splitter indicates the tip.

4. The device as recited in claim 1, wherein the one or more optical fibers are configured to indicate a start position where monitoring of the instrument begins, the start position including a sensor to confirm the start position, wherein the sensor includes at least one of an electromagnetic tracking sensor, a photoacoustic sensor and a marker.

5. The device as recited in claim 1, wherein the interventional instrument includes at least one of:
one or more rigid segments, and the one or more optical fibers are disposed within the one or more rigid segments: and
a joint and the one or more optical fibers are disposed within members connected by the joint.

6. The device as recited in claim 1, wherein the one or more optical fibers are disposed within a flexible sheet, the flexible sheet being coupled to the instrument for sensing a shape.

7. The device as recited in claim 1, wherein the instrument includes a volume-forming portion and the one or more optical fibers are bundled at poles for sensing a shape of the portion.

8. A system for shape sensing a medical instrument, comprising:
a processor;
a memory coupled to the processor;
one or more optical fibers coupled to the interventional instrument in a known geometric pattern on or about regions of articulation of an interventional instrument such that the known geometric pattern permits detection of shape tracking errors, the one or more optical fibers providing optical signals indicating an instantaneous change or current position or orientation of the instrument;
an optical interrogation module configured to interact with the one or more optical fibers to generate the optical signals; and
a shape determination module stored in memory and configured to determine location and shape of the instrument and compute shape tracking errors during a procedure based on the optical signals from the one or more optical fibers.

9. The system as recited in claim 8, wherein the one or more optical fibers include at least one of:
two segments on or in the instrument and the fiber segments are coupled with a splitter at a tip of the instrument such that an optical loss at the splitter indicates the tip: and
a fiber terminated at a tip of the instrument such that an optical loss in fiber indicates the tip.

10. The system as recited in claim 8, wherein the interventional instrument includes one or more rigid segments, and the one or more optical fibers are disposed within the one or more rigid segments.

11. The system as recited in claim 8, wherein the interventional instrument includes a joint and the one or more optical fibers are disposed within members connected by the joint.

12. The system as recited in claim 8, wherein the one or more optical fibers are disposed within a flexible sheet, the flexible sheet being coupled to the instrument for sensing shaping.

13. A method for shape sensing a medical device, comprising:
providing an interventional instrument having one or more regions of articulation with one or more optical fibers coupled to the interventional instrument in a known geometric pattern on or about the one or more regions of articulation of the instrument such that the known geometric pattern permits detection of shape tracking errors;
interrogating the one or more optical fibers to provide optical signals indicating an instantaneous change or current position or orientation of the instrument; and
interpreting the optical signals received to define the instantaneous change, current position or orientation of the instrument and the shape tracking errors.

14. The method as recited in claim 13, wherein providing includes at least one of:
providing one or more rigid segments, and the one or more optical fibers are disposed within the one or more rigid segments: and
providing a joint and the one or more optical fibers are disposed within members connected by the joint.

15. The method as recited in claim 13, wherein the one or more optical fibers are disposed within a flexible sheet, the flexible sheet being coupled to the instrument for sensing shape on the instrument.

* * * * *